United States Patent
Admati et al.

(10) Patent No.: US 11,717,660 B2
(45) Date of Patent: Aug. 8, 2023

(54) SILICON MICRONEEDLE STRUCTURE AND PRODUCTION METHOD

(71) Applicant: NanoPass Technologies Ltd., Ness Ziona (IL)

(72) Inventors: Gal Admati, Kibbutz Dorot (IL); Yotam Levin, Ness Ziona (IL); Yoav Hamisha, Mazkeret Batya (IL)

(73) Assignee: NANOPASS TECHNOLOGIES LTD., Ness Ziona (IL)

( * ) Notice: Subject to any disclaimer, the term of this patent is extended or adjusted under 35 U.S.C. 154(b) by 217 days.

(21) Appl. No.: 17/388,215

(22) Filed: Jul. 29, 2021

(65) Prior Publication Data
US 2023/0035272 A1    Feb. 2, 2023

(51) Int. Cl.
*A61M 37/00* (2006.01)

(52) U.S. Cl.
CPC ... *A61M 37/0015* (2013.01); *A61M 2037/003* (2013.01); *A61M 2037/0053* (2013.01); *A61M 2037/0061* (2013.01); *A61M 2207/00* (2013.01)

(58) Field of Classification Search
CPC ........ A61M 37/0015; A61M 2037/003; A61M 2037/0053; A61M 2037/0061; A61M 2207/00; A61M 2037/0023
See application file for complete search history.

(56) References Cited

U.S. PATENT DOCUMENTS

| | | |
|---|---|---|
| 6,533,949 B1 | 3/2003 | Yeshurun et al. |
| 7,588,552 B2 | 9/2009 | Yeshurun et al. |
| 7,648,484 B2 | 1/2010 | Yeshurun et al. |
| 7,850,657 B2 | 12/2010 | Yeshurun et al. |
| 7,998,119 B2 | 8/2011 | Yeshurun et al. |
| 8,007,466 B2 | 8/2011 | Yeshurun et al. |
| 8,454,844 B2 | 6/2013 | Yeshurun et al. |
| 10,828,429 B2 | 11/2020 | Admati et al. |
| 11,291,818 B2 | 4/2022 | Admati et al. |
| 2004/0098014 A1 | 5/2004 | Flugelman et al. |
| 2006/0051404 A1 | 3/2006 | Yeshurun et al. |
| 2008/0015516 A1 | 1/2008 | Lavi |
| 2008/0015522 A1 | 1/2008 | Yeshurun et al. |
| 2008/0091226 A1 | 4/2008 | Yeshurun et al. |

(Continued)

FOREIGN PATENT DOCUMENTS

| | | |
|---|---|---|
| AU | 2001282489 B2 | 6/2006 |
| CA | 2546443 A1 | 6/2005 |

(Continued)

*Primary Examiner* — Amber R Stiles
(74) *Attorney, Agent, or Firm* — Mark M. Friedman

(57) ABSTRACT

A microneedle structure has one or more microneedles (104) projecting from the major surface (102) of a substrate (100). The microneedle has a penetrating tip (106) formed at an intersection between upright surfaces (108) and an inclined surface (110) corresponding to a (1 1 1) crystallographic plane. The microneedle has an expanding portion bounded by a continuation of the upright surfaces (108) and inclined surface (110), and a constant cross-section portion bounded by a continuation of the upright surfaces and a slicing plane (112) extending from an edge (114) of inclined surface (110) towards, and perpendicular to, major surface (102) of the substrate. A width W of inclined surface (110) increases monotonically from penetrating tip (106) to edge (114).

20 Claims, 7 Drawing Sheets

(56) References Cited

U.S. PATENT DOCUMENTS

| | | |
|---|---|---|
| 2009/0011158 A1 | 1/2009 | Yeshurun |
| 2009/0012494 A1 | 1/2009 | Yeshurun et al. |
| 2009/0048557 A1 | 2/2009 | Yeshurun et al. |
| 2009/0054842 A1 | 2/2009 | Yeshurun et al. |
| 2009/0157094 A1 | 6/2009 | Yeshurun et al. |
| 2009/0247953 A1 | 10/2009 | Yeshurun et al. |
| 2010/0224590 A1 | 9/2010 | Yeshurun et al. |
| 2011/0282298 A1 | 11/2011 | Agian et al. |
| 2013/0110043 A1 | 5/2013 | Levin |
| 2013/0296791 A1 | 11/2013 | Segev et al. |
| 2014/0350514 A1 | 11/2014 | Levin |
| 2015/0038911 A1 | 2/2015 | Levin et al. |
| 2016/0184571 A1 | 6/2016 | Admati |
| 2018/0161563 A1* | 6/2018 | Renlund ............ A61B 10/0045 |
| 2018/0185623 A1 | 7/2018 | Lesher et al. |

FOREIGN PATENT DOCUMENTS

| | | |
|---|---|---|
| CA | 2420859 C | 4/2009 |
| EP | 1699524 A2 | 9/2006 |
| EP | 1330274 B1 | 11/2015 |
| IL | 13813100 | 10/2001 |
| JP | 2004507371 A | 3/2004 |
| JP | 2007511318 A | 5/2007 |
| WO | 2001066065 A2 | 3/2001 |
| WO | 2002017985 A2 | 3/2002 |
| WO | 2004035105 A2 | 4/2004 |
| WO | 2005049107 A2 | 6/2005 |
| WO | 2008072229 A2 | 6/2008 |
| WO | 2013061290 A1 | 5/2013 |
| WO | 2013114276 A2 | 8/2013 |

\* cited by examiner

SILICON MICRONEEDLE STRUCTURE AND PRODUCTION METHOD

FIELD AND BACKGROUND OF THE INVENTION

The present invention relates to microneedles and, in particular, it concerns a silicon microneedle structure and corresponding production methods.

Much interest has been shown in microneedles for a wide range of applications. As a replacement for hollow metal needles, hollow microneedles have potential to offer a wide range of advantages, including one or more of: painless or reduced-pain penetration, enhanced safety, reliable intradermal drug delivery, better control over delivery depth, lack of bending and blunting, and reduced needle visibility for patients with a fear of needles.

Silicon has been proposed as a material for microneedles due to its biocompatibility and the availability of well-developed, scalable manufacturing techniques similar to those used in MEMS. However, many proposed silicon microneedle designs have failed to achieve commercial success due to difficulties implementing a microneedle which is sufficiently sharp to penetrate the skin while at the same time being sufficiently robust to minimize risk of breakage during insertion.

A particularly effective hollow silicon microneedle structure has been developed by NanoPass Technologies Ltd. (Israel) and is commercially available under the tradename MICRONJET®. The microneedles are formed with upright walls perpendicular to an underlying substrate surface, and an oblique surface corresponding to a (1 1 1) crystallographic plane intersecting those walls so as to extend from a sharp penetrating tip to the substrate surface. This structure defines a generally triangular microneedle shape as viewed from the side, which provides a highly advantageous combination of a sharp penetrating tip and a robust needle body which is highly resistant to breaking. An example of such a needle is shown in the SEM image reproduced here as FIG. 5.

SUMMARY OF THE INVENTION

The present invention is a silicon microneedle structure and corresponding production methods.

According to the teachings of an embodiment of the present invention there is provided, a microneedle structure formed from a single crystal of silicon, the microneedle structure comprising: (a) a substrate having a major surface; (b) at least one microneedle integrally formed with the substrate so as to project from the major surface, the at least one microneedle comprising: (i) a penetrating tip formed at an intersection between at least one upright surface perpendicular to the major surface of the substrate and an inclined planar surface corresponding to a (1 1 1) crystallographic plane, (ii) an expanding portion bounded by a continuation of the at least one upright surface and the inclined surface, and (iii) a constant cross-section portion bounded by a continuation of the at least one upright surface and a slicing plane extending from an edge of the inclined surface towards, and perpendicular to, the major surface of the substrate, wherein a width of the inclined surface increases monotonically from the penetrating tip to the edge.

According to a further feature of an embodiment of the present invention, the constant cross-section portion extends for at least a fifth of a height of the penetrating tip from the major surface of the substrate.

According to a further feature of an embodiment of the present invention, a ratio of a height of the penetrating tip from the major surface of the substrate to a maximum dimension of the microneedle adjacent to the major surface is at least 1.6.

According to a further feature of an embodiment of the present invention, a ratio of a height of the penetrating tip from the major surface of the substrate to a maximum dimension of the microneedle adjacent to the major surface is at least 1.7.

According to a further feature of an embodiment of the present invention, a height of the penetrating tip from the major surface of the substrate is at least 750 microns, and wherein a maximum dimension of the microneedle parallel, and adjacent, to the major surface is no more than 500 microns.

According to a further feature of an embodiment of the present invention, a height of the penetrating tip from the major surface of the substrate is at least 800 microns, and wherein a maximum dimension of the microneedle parallel, and adjacent, to the major surface is no more than 450 microns.

According to a further feature of an embodiment of the present invention, a cross-section taken through the constant cross-section portion of the microneedle parallel to the major surface of the substrate has a length dimension perpendicular to the slicing plane and a width parallel to the slicing plane, the length being at least 50% greater than the width.

According to a further feature of an embodiment of the present invention, the at least one upright surface adjacent to the penetrating tip comprises a first planar surface and a second planar surface smoothly linked by an arcuate surface, the first and second planar surfaces being symmetrically deployed on opposite sides of a center plane passing through the microneedle and forming between them an angle of between 45 degrees and 75 degrees.

According to a further feature of an embodiment of the present invention, the arcuate surface has a radius of curvature between 10 microns and 40 microns.

According to a further feature of an embodiment of the present invention, the at least one upright surface further comprises a third planar surface and a fourth planar surface arranged symmetrically on opposite sides of the center plane, the third and fourth planar surfaces forming between them of between 5 degrees and 25 degrees.

According to a further feature of an embodiment of the present invention, there is also provided a bore extending from the inclined surface through the expanding portion, through the constant cross-section portion and through the substrate to a rear surface of the substrate.

According to a further feature of an embodiment of the present invention, the slicing plane is also an edge of the substrate.

According to a further feature of an embodiment of the present invention, the at least one microneedle is implemented as a plurality of microneedles integrally formed with the substrate, the plurality of microneedles having co-planar slicing planes.

There is also provided according to the teachings of an embodiment of the present invention, a method for manufacturing a microneedle structure, the method comprising the steps of: (a) providing a microneedle device precursor formed from a single crystal of silicon and comprising: (i) a substrate having a major surface, (ii) at least one microneedle integrally formed with the substrate so as to project from the major surface, the at least one microneedle comprising: (A) a penetrating tip formed at an intersection between at least one upright surface perpendicular to the major surface of the substrate and an inclined planar surface corresponding to a (1 1 1) crystallographic plane, and (B) an expanding portion bounded by a continuation of the at least one upright surface and the inclined surface, the inclined surface extending to the major surface of the substrate; and (b) slicing the microneedle device precursor along a slicing plane perpendicular to the major surface of the substrate and passing through the inclined surface of the microneedle and through at least part of the substrate so as to generate a constant cross-section portion bounded by a continuation of the at least one upright surface and the slicing plane extending from an edge of the inclined surface towards the major surface of the substrate.

According to a further feature of an embodiment of the present invention, the slicing is performed so that the constant cross-section portion extends for at least a fifth of a height of the penetrating tip from the major surface of the substrate.

According to a further feature of an embodiment of the present invention, the slicing is performed so that a ratio of a height of the penetrating tip from the major surface of the substrate to a maximum dimension of the microneedle adjacent to the major surface is at least 1.6.

According to a further feature of an embodiment of the present invention, the slicing is performed so that a ratio of a height of the penetrating tip from the major surface of the substrate to a maximum dimension of the microneedle adjacent to the major surface is at least 1.7.

According to a further feature of an embodiment of the present invention, the slicing is performed as part of a dicing process for separating the substrate into a plurality of chips each containing a microneedle structure.

According to a further feature of an embodiment of the present invention, the slicing is performed by a process or combination of processes selected from the group consisting of: mechanical cutting; laser cutting; plasma cutting; and DRIE.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a silicon microneedle structure and corresponding production methods.

The principles and operation of silicon microneedle structures according to the present invention may be better understood with reference to the drawings and the accompanying description.

By way of introduction, the aforementioned microneedles from NanoPass Technologies Ltd. have been found to be highly advantageous as mentioned above for their combination of sharpness together with structural robustness provided by the triangular form as viewed laterally, formed between the oblique (1 1 1) surface and the other vertical surfaces. However, the fixed geometry of the (1 1 1) oblique surface imposes certain design limitations which are unsuitable for certain applications, particularly in cases where relatively tall microneedles are required. Specifically, the (1 1 1) plane forms a well-defined angle of $\tan^{-1}(\sqrt{2})$, which is 54.7 degrees to the substrate surface. As a result, the maximum dimension of the base of the conventional microneedle, corresponding to the size of the skin wound caused by penetration, increases linearly as a function of the microneedle height. For larger microneedles (e.g., intended for penetration depths over about 750 microns), this may result in an unnecessarily large skin wound, with corresponding tissue damage, reduced penetration efficacy and increased propensity for post-injection leakage. This is particularly important not only for the skin, but also for various biological barriers such as the eye. The present invention provides a modification to the earlier design, which maintains the main features of sharpness, robustness and design flexibility of bore shape and position independent of outer structure contour, while at the same time allowing reduction of the microneedle base dimensions, and consequently reducing tissue trauma, increasing penetration efficacy and reducing leakage caused by penetration of the microneedle.

Figure 1A:
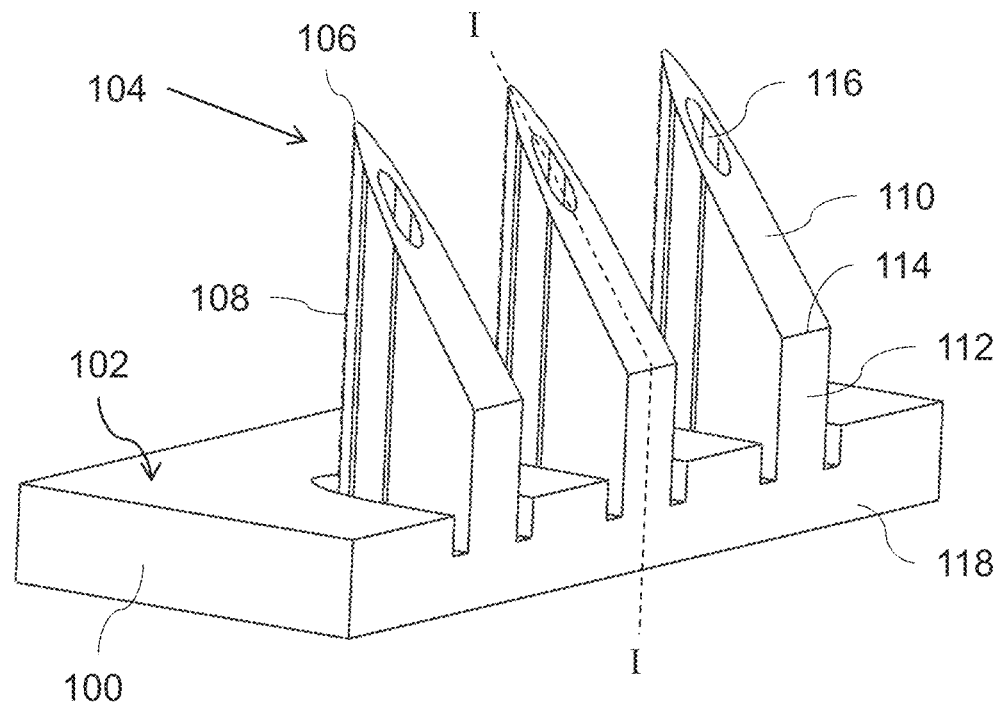
FIG. 1A is an isometric view of a microneedle structure, constructed and operative according to the teachings of an embodiment of the present invention.
Figure 1B:
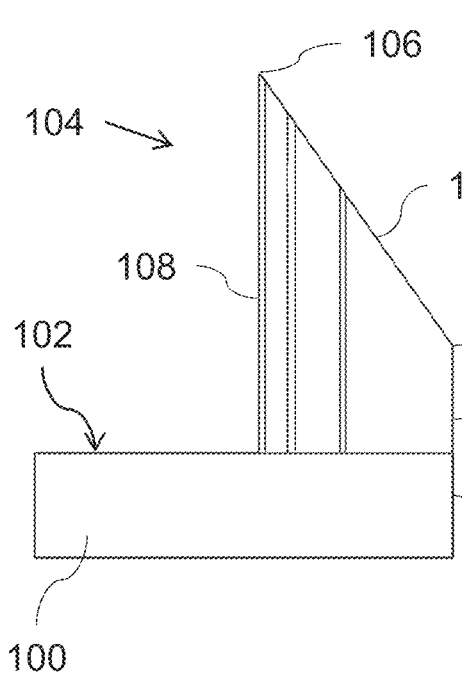
FIGS. 1B, 1D and 1E are side, front and top views, respectively, of the microneedle structure of FIG. 1A.
Figure 1C:
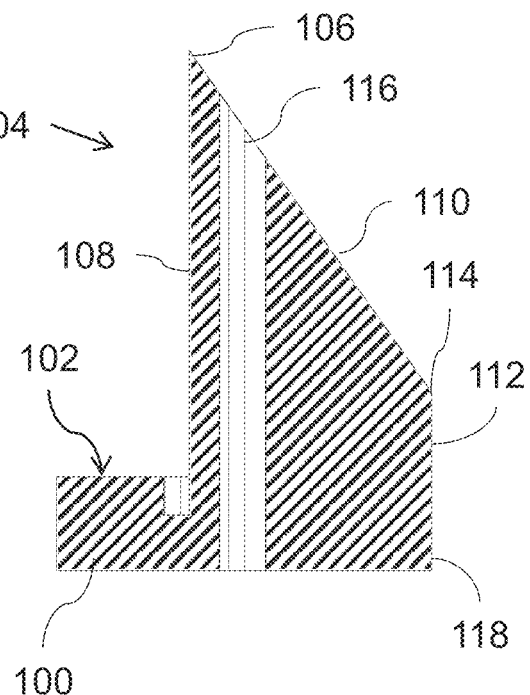
FIG. 1C is a cross-sectional view taken along plane I-I of FIG. 1A.
Figure 1D:
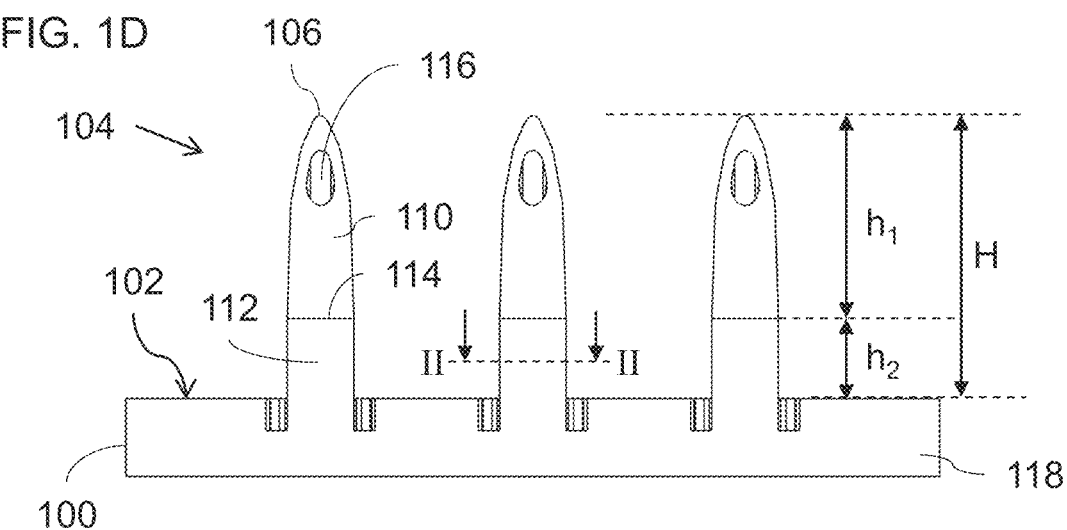

Referring now to the drawings, FIGS. 1A-1F and 2A-2B illustrate two variants of a microneedle structure, constructed and operative according to the principles of an embodiment of the present invention, formed from a single crystal of silicon. The microneedle structure includes a substrate 100 having a major surface 102 from which at least one, and in this non-limiting example three, integrally formed microneedles 104 project. Each microneedle 104 has a penetrating tip 106 formed at an intersection between at least one upright surface 108 perpendicular to the major surface of the substrate and an inclined planar surface 110, corresponding to a (1 1 1) crystallographic plane (defined by Miller indices). Each microneedle has an expanding portion, corresponding to height $h_1$ illustrated in FIG. 1D, bounded by a continuation of the at least one upright surface 108 and inclined surface 110. A constant cross-section portion, corresponding to height $h_2$ in FIG. 1D, is bounded by a continuation of the at least one upright surface 108 and a slicing plane 112 extending from an edge 114 of inclined surface 110 towards, and perpendicular to, major surface 102 of substrate 100. A width W of inclined surface 110 increases monotonically from penetrating tip 106 to edge 114.

At this stage, it will already be apparent that the structure of microneedle 104 provides profound advantages. Specifically, the expanding portion of the microneedle provides particularly advantageous properties of a sharp penetrating tip in combination with a robust microneedle body, while the presence of the constant cross-section portion provides an additional degree of design freedom to reduce the base dimensions of the microneedle for a given microneedle height so as to increase penetration efficacy and limit skin trauma at the site of penetration.

In a sense, the microneedle structure defined herein may be considered as providing an increased aspect ratio compared to the prior NanoPass microneedle design. Specifically, the design based on a (1 1 1) plane extending to the substrate is inherently limited by the 54.7-degree angle to an aspect ratio of about 1.4 (where the term "aspect ratio" is used to refer to the ratio between the microneedle overall height from the substrate surface and the largest dimension of the microneedle measured adjacent and parallel to the surface of the substrate). In contrast, various particularly preferred implementations of the present invention have an aspect ratio of at least 1.6, and more preferably 1.7.

As a result of this structure, the microneedles of the present invention may advantageously achieve an overall microneedle height of at least 750 microns while maintaining a maximum dimension of the microneedle parallel, and adjacent, to the major surface of no more than about 500 microns, and in certain particularly preferred cases, an overall microneedle height of at least 800 microns while maintaining a maximum dimension of the microneedle parallel, and adjacent, to the major surface of no more than 450 microns.

To achieve optimal benefit from the constant cross-section portion of the microneedle, the constant cross-section portion preferably extends for a height $h_2$ of at least about a fifth of the overall height H of the penetrating tip from the major surface of the substrate.

Figure 1E:
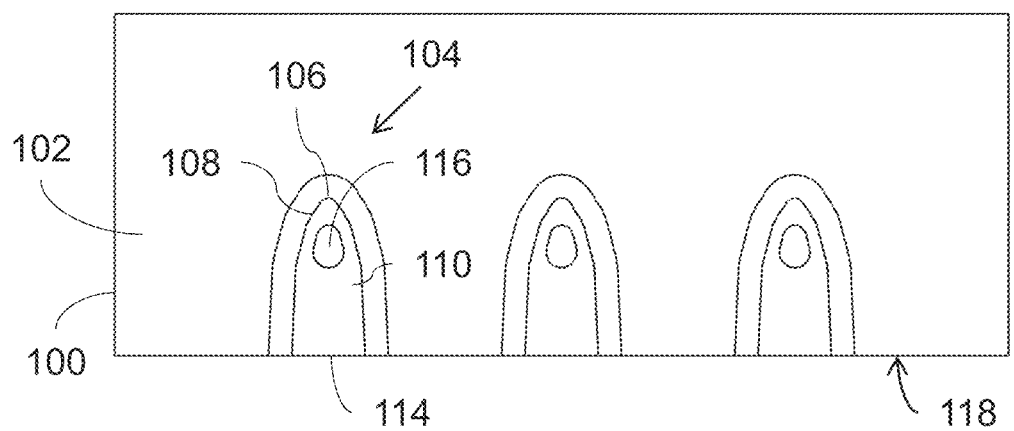
Figure 1F:
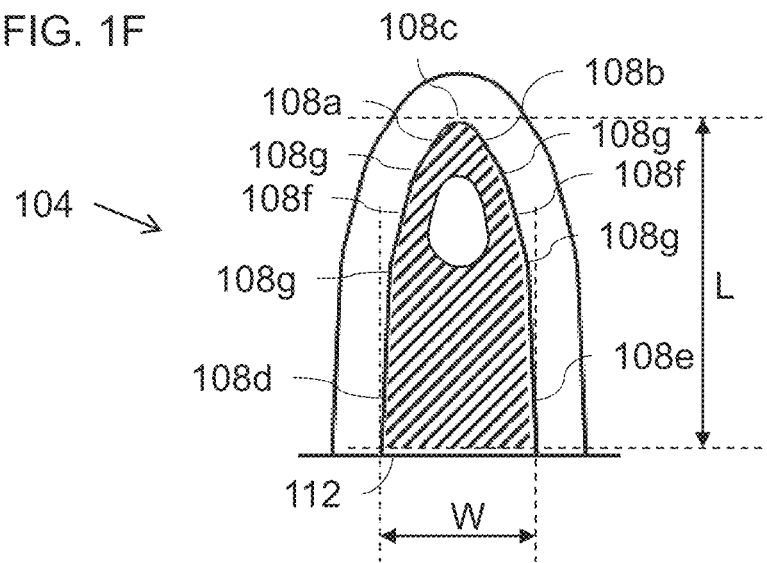
FIG. 1F is a cross-sectional view taken along plane II-II of FIG. 1D.

A preferred but non-limiting shape of the base of microneedle 104 can best be seen in the top view of FIG. 1E and, in greater detail, in the enlarged cross-sectional view of FIG. 1F. As seen here, in a cross-section taken through the constant cross-section portion of the microneedle parallel to the major surface of the substrate, a length dimension L perpendicular to slicing plane 112 is preferably at least 50% greater than a width W parallel to slicing plane 12 (i.e., a length-to-width ratio of at least 1.5), and most preferably has a length-to-width ratio of between about 1.8 and about 2.2.

The at least one upright surface 108 preferably defines an outline of the microneedle cross-section which is symmetrical about a central plane, corresponding to the cross-section plane I-I denoted in FIG. 1A. In order to provide a particularly preferred geometry for the penetrating tip, the adjacent regions of the at least one upright surface 108 preferably include a first planar surface 108a and a second planar surface 108b smoothly linked by an arcuate surface 108c, with first and second planar surfaces 108a and 108b symmetrically deployed on opposite sides of the center plane of symmetry and forming between them an angle of between 45 degrees and 75 degrees. Arcuate surface 108c preferably has a radius of curvature of between 10 microns and 40 microns. These parameters, together with the inclined planar surface 110, have been found to provide a particularly advantageous balance between sufficient sharpness to achieve effective penetration while providing sufficient robustness to minimize breakage and wear of the tips under a wide range of operating conditions.

In order to achieve the aforementioned length-to-width ratio, the at least one upright surface preferably further includes at least a third planar surface 108d and a fourth planar surface 108e arranged symmetrically on opposite sides of the center plane, and forming between them an angle of less than 30 degrees, and preferably between 5 degrees and 25 degrees. In order to avoid any pronounced edges along the sides of the microneedle, the particularly preferred implementation illustrate here features an additional pair of planar surface segments 108f connected to the adjacent surfaces by rounded transitions regions 108g. A similar effect could be achieved by linking surfaces 108a and 108d and surface 108b and 108e through a large-radius curved connecting portion (not shown).

When reference is made here to an angle formed between two surfaces which do not themselves meet, the angle is taken to be the angle between the planes of those surfaces if continued until they meet.

The present invention relates primarily, although not exclusively, to hollow microneedle structures suitable for delivering flowable compositions into the skin and/or for sampling fluids from the body. To this end, microneedles 104 preferably also include a bore 116 extending from inclined surface 110 through the expanding portion, through the constant cross-section portion and through substrate 100 to a rear surface of the substrate (see FIG. 1C). In the particularly preferred implementations illustrated here, bore 116 is located in the half of inclined surface 110 closest to the penetrating tip 106, thereby ensuring effective sealing of the open area of the bore within tissue during an early stage of penetration. In alternative implementations (not shown), bore 116 may have an elongated cross-sectional shape which extends across a major portion of the length of inclined surface 110, with effective sealing being achieved when the microneedle penetrates tissue sufficiently for the tissue to pass beyond edge 114 and surround the constant cross-section portion of the microneedle.

While the microneedle structure described herein may be implemented in an arbitrary location on the surface of a substrate, certain particularly preferred implementations have the microneedle located adjacent to an edge of the substrate. In this case, according to one particularly preferred set of implementations, slicing plane 112 is coplanar with an edge 118 of substrate 100. Although the present invention may be implemented using a single microneedle, particularly preferred implementations, such as those illustrated here, employ a plurality of microneedles, typically in a row (linear array) as shown. Thus, one particularly preferred embodiment as illustrated here has at least three hollow microneedles 204 in a linear array of microneedles integrally formed with substrate 100, with the slicing planes 112 of all of the microneedles co-planar with each other, and with edge 118 of substrate 100. The use of a slicing plane which is coplanar with an edge of the final substrate is particularly suited to a production method in which both the slicing plane and the substrate edge are formed in a single cutting operation, such as during a dicing process during manufacture of the microneedle chips. This will be described further below.

Figure 2A:
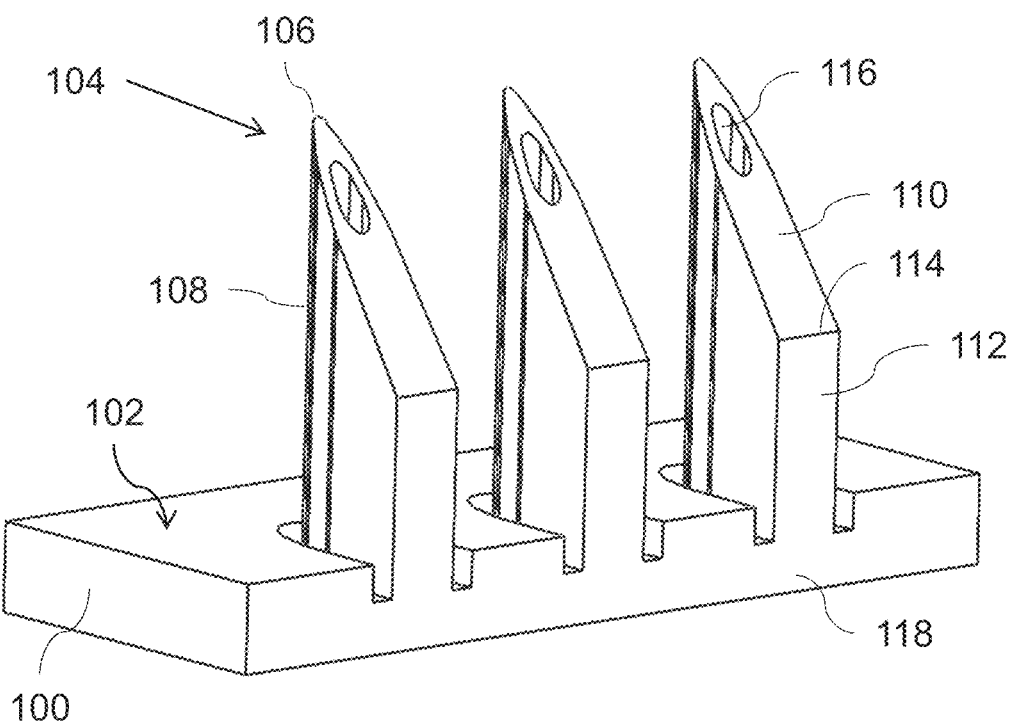
FIGS. 2A and 2B are views similar to FIGS. 1A and 1B, respectively, of a variant implementation of the microneedle structure.
Figure 2B:
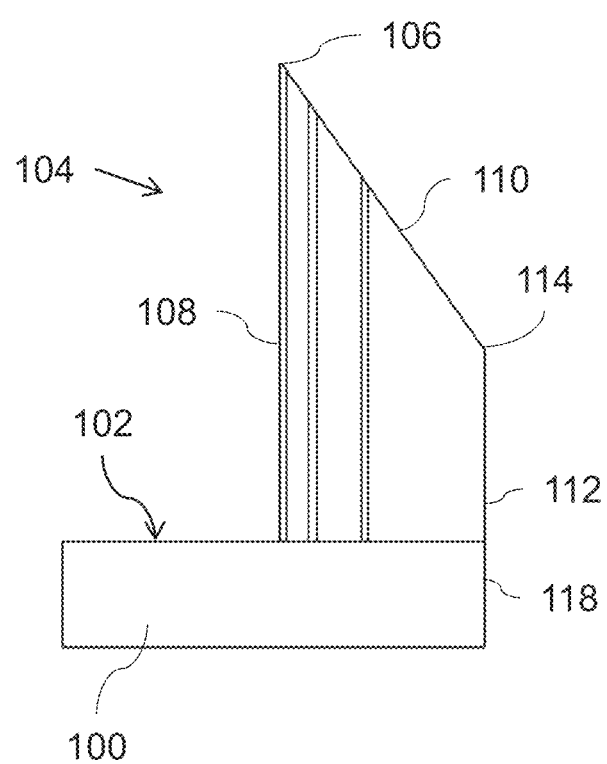

The use of a constant cross-section portion in the microneedle structure provides considerable design freedom to implement microneedles of differing heights while separately selecting the desired base dimensions. By way of non-limiting examples, the microneedles of FIGS. 1A-1F may advantageously be implemented with an overall height H of 750-850 microns, a base length L of 380-450 microns and a base width W of 180-220 microns. The microneedles of FIGS. 2A and 2B employ a longer constant cross-section portion together with other parameters that are generally similar to that of FIGS. 1A-1F to implement microneedles with an overall height H of 900-1100 microns, a base length L of 380-450 microns and a base width W of 180-220 microns. In all other respects, the microneedle structure of FIGS. 2A and 2B is analogous in structure and function to that of FIGS. 1A-1F. It should be noted that the microneedles of the present invention are not limited to the above ranges of heights, and that the advantageous geometrical properties of the structure described may also be implemented in smaller microneedles, typically from around 600 microns height upwards, and in larger microneedles, for example, up to 1500 microns, or in some cases, 2 millimeters height or more.

Figure 3:
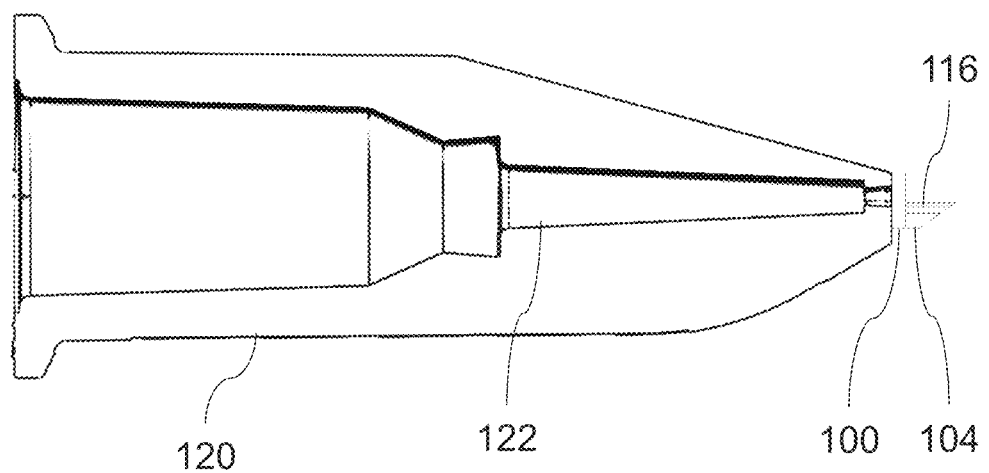
FIG. 3 is a schematic longitudinal axial cross-sectional view taken through a microneedle adapter employing the microneedle structure of FIG. 1A.
Figure 4A:
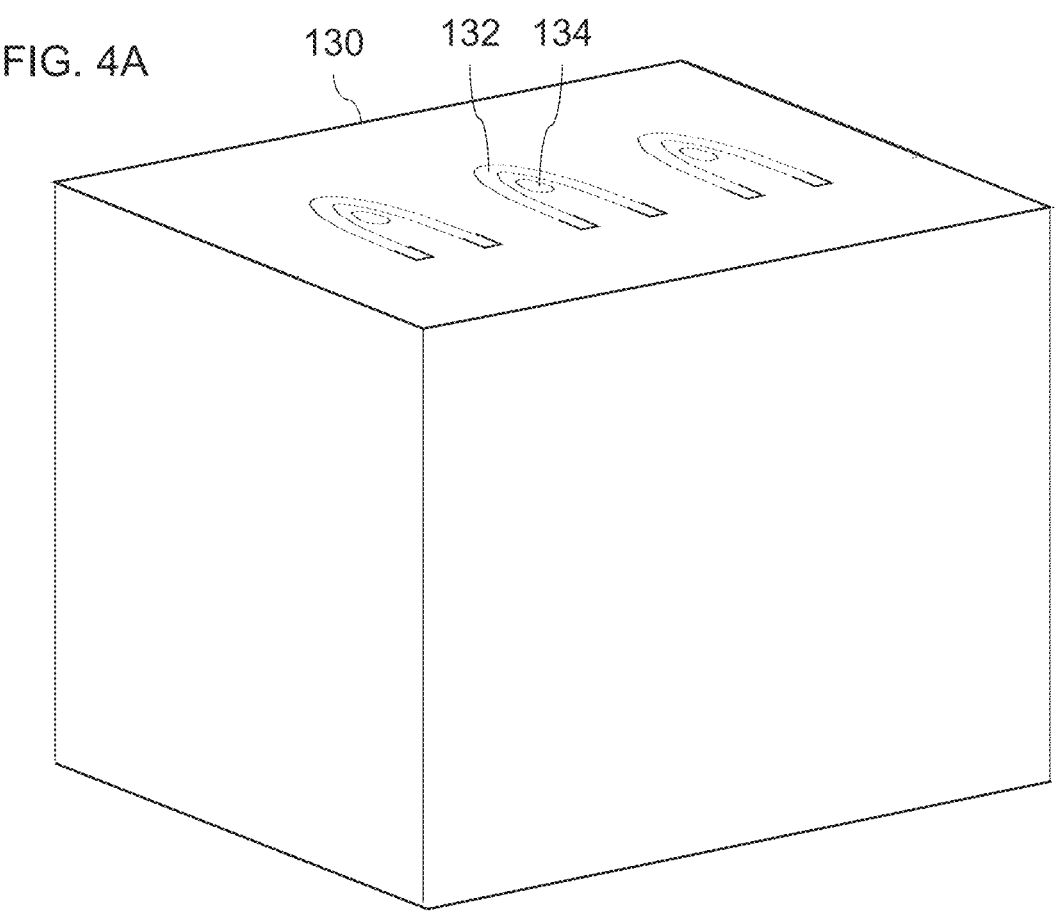
FIG. 4A shows schematically a silicon crystal wafer during production of the microneedle structure of FIG. 1A.
Figure 4B:
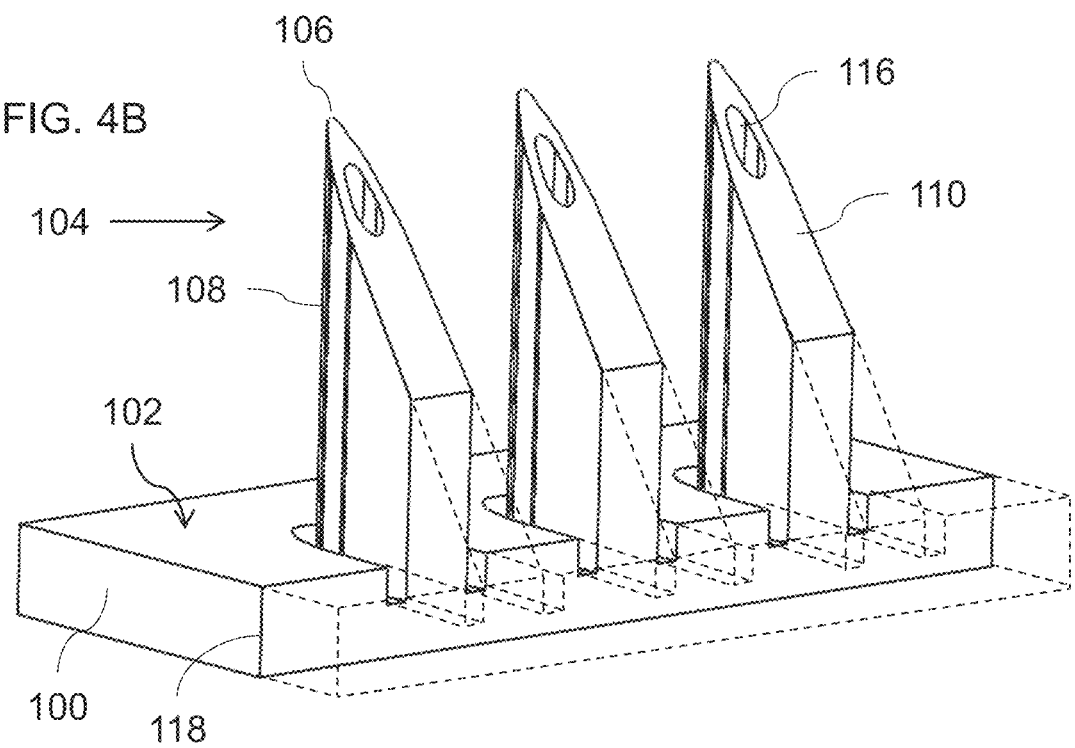
FIGS. 4B and 4C are an isometric view and a side view, respectively, of a microneedle device precursor formed from the wafer of FIG. 4A.
Figure 4C:
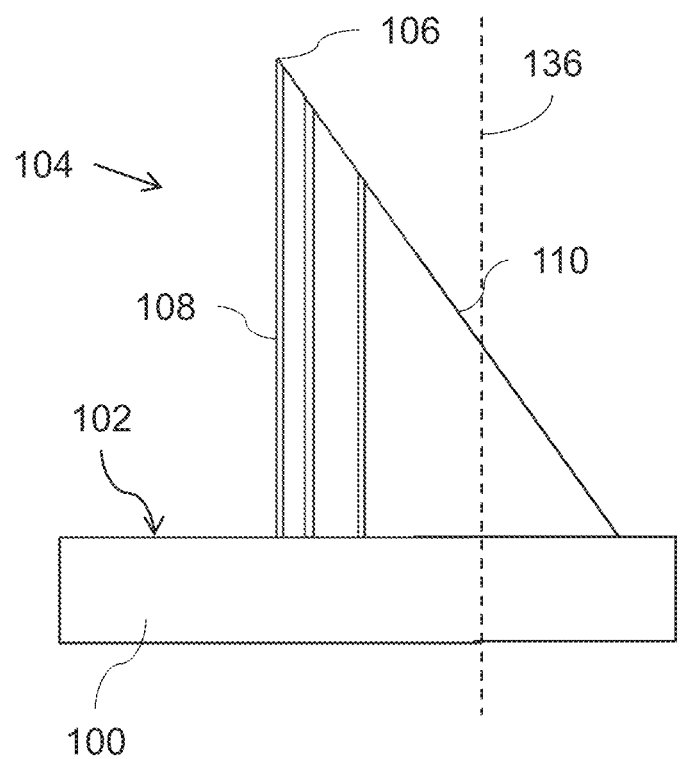
Figure 4D:
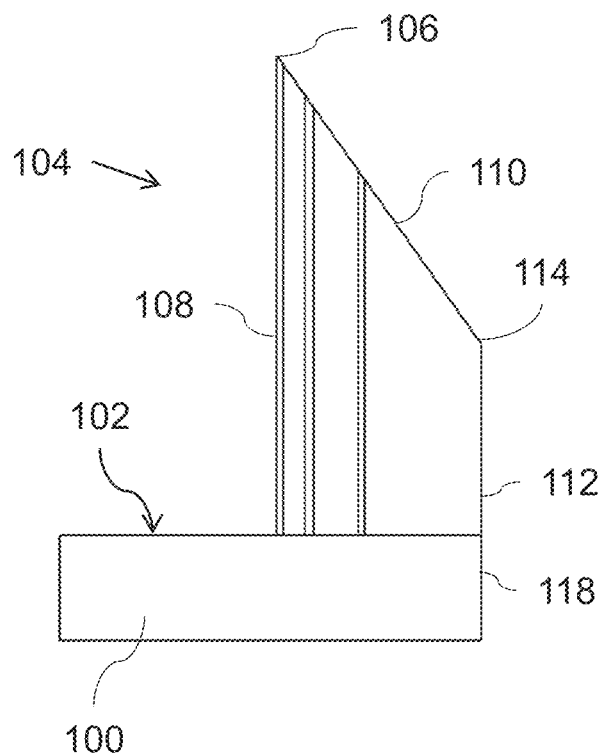
FIG. 4D is a side view of the microneedle structure formed by slicing the microneedle device precursor of FIG. 4C along slicing plane 136.
Figure 5:
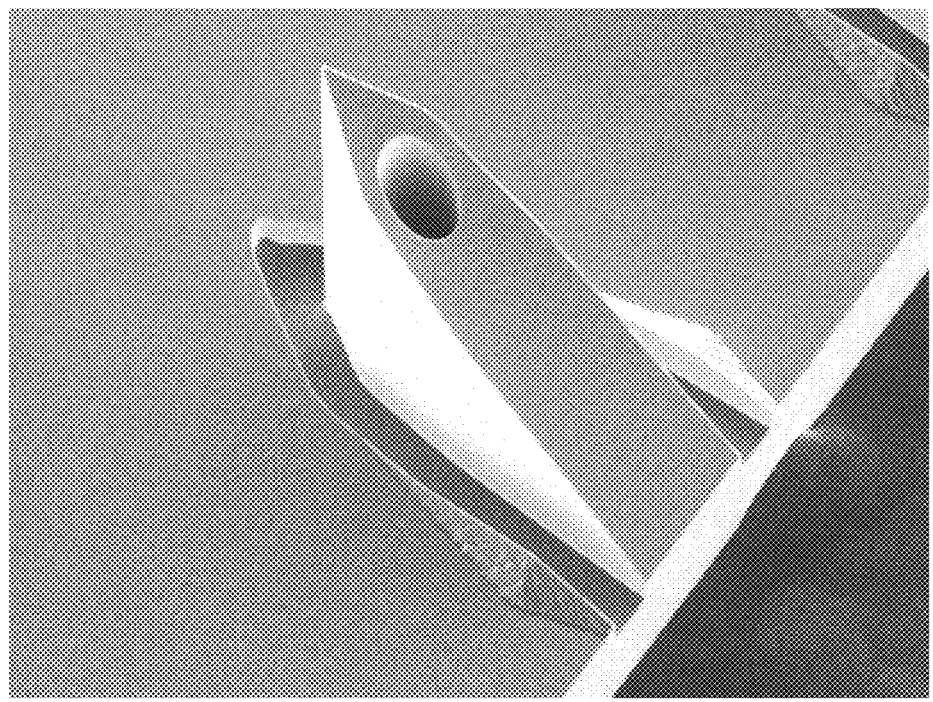
FIG. 5 (described above) is a scanning electron microscope image of a microneedle manufactured by NanoPass Technologies Ltd.

FIG. 3 shows schematically a typical mode of use of the microneedle structures of the present invention as part of a device. In this example, the substrate 100 is attached to a syringe adapter 120 that is formed with a female Luer interface for mating with a syringe or other fluid flow system connection. A flow channel 122 passes through the adapter to supply fluid to the rear face of substrate 100 for delivery via bores 116. Adapter 120 is only one of a large number of examples of possible applications of the microneedle structure. Other non-limiting examples include microneedle structures that are integrated with disposable prefilled syringes, microneedles integrated with drug delivery patches and pumps, microneedle pen needle adaptations for pen injector systems, auto injector systems and a wide range of other applications.

Turning now to a method for manufacturing the microneedle structure of the present invention, which is in itself also an embodiment of a method according to an aspect of the present invention, this may advantageously be implemented by first producing microneedles with inclined surface 110 extending to the substrate surface, and then performing a cutting operation (also referred to as "slicing" or "dicing") to generate slicing plane 112, and preferably also substrate edge 118, to provide the final microneedle structures as illustrated.

The entire production process is explained here schematically with reference to FIGS. 4A-4D. Firstly, a silicon single crystal wafer 130 is processed, typically by a dry etching process, such as deep reactive ion etching (DRIE), to generate trenches 132 corresponding on the inner side to the desired shape of the upright surfaces 108 of the final microneedle structure, and bores 134 corresponding to the position and shape of the bores 116 of the final microneedle structures. These patterns are typically repeated patterns formed in spaced relation across the surface of a wafer, typically with hundreds or even thousands of such configurations per wafer. The internal dimensions of bore 134 are preferably greater than the width of trenches 132, such that the DRIE processing reaches a greater depth for bores 134 than for trenches 132. This facilitates completion of the length of the bore through the entire thickness of the wafer (typically at a later stage of the processing), either through the front-side DRIE processing itself or by a corresponding DRIE process or other drilling process (e.g., laser cutting) forming a complementary bore from the back side of the wafer to meet bores 134.

The internal surfaces of trenches 132 and bores 134 are then coated with a protective layer. An anisotropic wet etch is then performed. This lowers the exposed surface of the top of the wafer evenly (the (1 0 0) "horizontal" plane) in regions outside the trenches 132 to form major surface 102, while eroding the regions partially circumscribed by trenches 132 on the (1 1 1) plane. Once the desired height H of the microneedles has been exposed, the protective coatings are removed to reveal a microneedle device precursor with an inclined surface extending all the way down to the upper surface of the substrate, as indicated in the dashed-line structure of FIG. 4B and the side view of FIG. 4C. As before, the schematic illustrations show this structure as a free-standing structure with one set of microneedles, but the structure is more preferably manufactured up to this stage as part of an extended wafer which includes many such structures.

The microneedle structure is then completed by slicing the microneedle device precursor along a slicing plane 136 (FIG. 4C) perpendicular to the major surface 102 of substrate 100 and passing through the inclined surface of the microneedle and through the substrate so as to generate a constant cross-section portion bounded by a continuation of the at least one upright surface 108 and the slicing plane 136 extending from an edge 114 of the inclined surface 110 towards the major surface 102 of substrate 100. This slicing step may be performed by any suitable cutting technique, including mechanical cutting or dicing, plasma and laser cutting. A process in which an additional dry etching step (DRIE) is used to form the slicing plane 136 also falls within the scope of the present invention, and may be preferred in a case in which the microneedle is to be formed at a location spaced away from an edge of the substrate. In certain particularly preferred implementations, the slicing is performed as part of a dicing operation in which the overall wafer is separated into multiple sections of substrate each with its own set of at least one, and preferably three, microneedles, as illustrated. The position of the slicing is chosen in order to generate the various preferred parameters of the proportions, aspect ratio etc. as described above, such as having the constant cross-section portion extend for at least a fifth of a height of the penetrating tip from the major surface of the substrate, and having an aspect ratio of at least 1.6, and more preferably at least 1.7.

It will be appreciated that the above descriptions are intended only to serve as examples, and that many other embodiments are possible within the scope of the present invention as defined in the appended claims.

What is claimed is:

1. A microneedle structure formed from a single crystal of silicon, the microneedle structure comprising:
   (a) a substrate having a major surface;
   (b) at least one microneedle integrally formed with said substrate so as to project from said major surface, said at least one microneedle comprising:
      (i) a penetrating tip formed at an intersection between at least one upright surface perpendicular to said major surface of said substrate and a planar inclined surface corresponding to a (1 1 1) crystallographic plane,
      (ii) an expanding portion bounded by a continuation of said at least one upright surface and said inclined surface, and
      (iii) a constant cross-section portion bounded by a continuation of said at least one upright surface and a slicing plane extending from an edge of said inclined surface towards, and perpendicular to, said major surface of said substrate,
   wherein a width of said inclined surface increases monotonically from said penetrating tip to said edge, and wherein said slicing plane is also an edge of said substrate.

2. The microneedle structure of claim 1, wherein said constant cross-section portion extends for at least a fifth of a height of said penetrating tip from said major surface of said substrate.

3. The microneedle structure of claim 1, wherein a ratio of a height of said penetrating tip from said major surface of said substrate to a maximum dimension of said microneedle adjacent to said major surface is at least 1.6.

4. The microneedle structure of claim 1, wherein a ratio of a height of said penetrating tip from said major surface of said substrate to a maximum dimension of said microneedle adjacent to said major surface is at least 1.7.

5. The microneedle structure of claim 1, wherein a height of said penetrating tip from said major surface of said substrate is at least 750 microns, and wherein a maximum dimension of said microneedle parallel, and adjacent, to said major surface is no more than 500 microns.

6. The microneedle structure of claim 1, wherein a height of said penetrating tip from said major surface of said substrate is at least 800 microns, and wherein a maximum dimension of said microneedle parallel, and adjacent, to said major surface is no more than 450 microns.

7. The microneedle structure of claim 1, wherein a cross-section taken through said constant cross-section portion of said microneedle parallel to said major surface of said substrate has a length dimension perpendicular to said slicing plane and a width parallel to said slicing plane, said length being at least 50% greater than said width.

8. The microneedle structure of claim 1, wherein said at least one upright surface adjacent to said penetrating tip comprises a first planar surface and a second planar surface smoothly linked by an arcuate surface, said first and second planar surfaces being symmetrically deployed on opposite sides of a center plane passing through said microneedle and forming between them an angle of between 45 degrees and 75 degrees.

9. The microneedle structure of claim 8, wherein said arcuate surface has a radius of curvature between 10 microns and 40 microns.

10. The microneedle structure of claim 8, wherein said at least one upright surface further comprises a third planar surface and a fourth planar surface arranged symmetrically on opposite sides of said center plane, said third and fourth planar surfaces forming between them of between 5 degrees and 25 degrees.

11. The microneedle structure of claim 1, further comprising a bore extending from said inclined surface through said expanding portion, through said constant cross-section portion and through said substrate to a rear surface of said substrate.

12. The microneedle structure of claim 1, wherein said at least one microneedle is implemented as a plurality of microneedles integrally formed with said substrate, said plurality of microneedles having co-planar slicing planes.

13. A method for manufacturing a microneedle structure, the method comprising the steps of:
(a) providing a microneedle device precursor formed from a single crystal of silicon and comprising:
(i) a substrate having a major surface,
(ii) at least one microneedle integrally formed with said substrate so as to project from said major surface, said at least one microneedle comprising:
(A) a penetrating tip formed at an intersection between at least one upright surface perpendicular to said major surface of said substrate and a planar inclined surface corresponding to a (1 1 1) crystallographic plane, and
(B) an expanding portion bounded by a continuation of said at least one upright surface and said inclined surface, said inclined surface extending to said major surface of said substrate; and
(b) slicing said microneedle device precursor along a slicing plane perpendicular to said major surface of said substrate and passing through said inclined surface of said microneedle and through at least part of said substrate so as to generate a constant cross-section portion bounded by a continuation of said at least one upright surface and said slicing plane extending from an edge of said inclined surface towards said major surface of said substrate.

14. The method of claim 13, wherein said slicing is performed so that said constant cross-section portion extends for at least a fifth of a height of said penetrating tip from said major surface of said substrate.

15. The method of claim 13, wherein said slicing is performed so that a ratio of a height of said penetrating tip from said major surface of said substrate to a maximum dimension of said microneedle adjacent to said major surface is at least 1.6.

16. The method of claim 13, wherein said slicing is performed so that a ratio of a height of said penetrating tip from said major surface of said substrate to a maximum dimension of said microneedle adjacent to said major surface is at least 1.7.

17. The method of claim 13, wherein said slicing is performed as part of a dicing process for separating said substrate into a plurality of chips each containing a microneedle structure.

18. The method of claim 13, wherein said slicing is performed by a process or combination of processes selected from the group consisting of: mechanical cutting; laser cutting; plasma cutting; and DRIE.

19. A microneedle structure formed from a single crystal of silicon, the microneedle structure comprising:
(a) a substrate having a major surface;
(b) at least one microneedle integrally formed with said substrate so as to project from said major surface, said at least one microneedle comprising:
(i) a penetrating tip formed at an intersection between at least one upright surface perpendicular to said major surface of said substrate and a planar inclined surface corresponding to a (1 1 1) crystallographic plane,
(ii) an expanding portion bounded by a continuation of said at least one upright surface and said inclined surface, and
(iii) a constant cross-section portion bounded by a continuation of said at least one upright surface and a slicing plane extending from an edge of said inclined surface towards, and perpendicular to, said major surface of said substrate,
wherein a width of said inclined surface increases monotonically from said penetrating tip to said edge,
and wherein said at least one upright surface adjacent to said penetrating tip comprises a first planar surface and a second planar surface smoothly linked by an arcuate surface, said first and second planar surfaces being symmetrically deployed on opposite sides of a center plane passing through said microneedle and forming between them an angle of between 45 degrees and 75 degrees.

20. The microneedle structure of claim 19, wherein said at least one upright surface further comprises a third planar surface and a fourth planar surface arranged symmetrically on opposite sides of said center plane, said third and fourth planar surfaces forming between them of between 5 degrees and 25 degrees.

* * * * *